(12) United States Patent
Ivanov et al.

(10) Patent No.: US 7,952,475 B2
(45) Date of Patent: May 31, 2011

(54) COMMUNICATION SYSTEM FOR MONITORING THE HEALTH STATUS OF A PATIENT, COMMUNICATION DEVICE, SENSOR DEVICE AND METHOD

(75) Inventors: Eugene Ivanov, Eindhoven (NL); Wim Stut, Eindhoven (NL); Frank Wartena, Den Bosch (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 377 days.

(21) Appl. No.: 12/300,639

(22) PCT Filed: May 8, 2007

(86) PCT No.: PCT/IB2007/051717
§ 371 (c)(1),
(2), (4) Date: Nov. 13, 2008

(87) PCT Pub. No.: WO2007/135588
PCT Pub. Date: Nov. 29, 2007

(65) Prior Publication Data
US 2009/0128325 A1 May 21, 2009

(30) Foreign Application Priority Data
May 16, 2006 (EP) .................................. 06113976

(51) Int. Cl.
*G08B 1/08* (2006.01)
*G08B 23/00* (2006.01)
*A61B 5/00* (2006.01)

(52) U.S. Cl. ........... 340/539.12; 340/539.21; 340/573.1; 340/507; 600/300; 600/301; 128/903; 128/904; 706/924; 705/2

(58) Field of Classification Search ............. 340/539.12; 600/301; 128/903; 706/924
See application file for complete search history.

(56) References Cited

U.S. PATENT DOCUMENTS

| | | |
|---|---|---|
| 5,416,695 A | 5/1995 | Stutman et al. |
| 5,959,529 A | 9/1999 | Kail, IV |
| 2002/0156384 A1 | 10/2002 | Eggers et al. |
| 2004/0236188 A1 | 11/2004 | Hutchinson et al. |
| 2004/0236189 A1 | 11/2004 | Hawthorne et al. |
| 2004/0249249 A1 | 12/2004 | Lawson et al. |
| 2005/0038332 A1 | 2/2005 | Saidara et al. |
| 2005/0151640 A1 | 7/2005 | Hastings |

FOREIGN PATENT DOCUMENTS
WO 03009207 A1 1/2003

*Primary Examiner* — Donnie L Crosland
(74) *Attorney, Agent, or Firm* — Larry Liberchuk

(57) ABSTRACT

A communication system for monitoring the health status of a patient includes a communication device and a sensor device, the communication device comprising a first communication interface for communication with the sensor device and comprising a second communication interface for communication with a health care center, the communication device being able to generate a warning message upon failure of either the first communication interface or the second communication interface, wherein the generation of a warning message is prevented if the failure of the first communication interface begins and ends during a first time interval and/or the generation of a warning message is prevented if the failure of the second communication interface begins and ends during a third time interval and/or the communication device comprises a detection device for detecting a critical or non-critical health status, and the generation of a warning message is prevented if both the duration of failure of the second communication interface is shorter than a second time interval and a non-critical health status is detected.

14 Claims, 1 Drawing Sheet

COMMUNICATION SYSTEM FOR MONITORING THE HEALTH STATUS OF A PATIENT, COMMUNICATION DEVICE, SENSOR DEVICE AND METHOD

The present invention relates to a communication system for monitoring the health status of a patient. The present invention further relates to a communication device, a sensor device and a method of monitoring the health status of a patient.

Advances in sensor technology, electronics, and communications have made it possible for physiological characteristics of patients to be monitored even when the patients are ambulatory and not in continuous, direct contact with a hospital monitoring system. Personal health systems may consist of multiple connected devices that collect and process data on a person's health. For example, a heart rate sensor device worn by the patient produces heart rate information and sends it to the patient's cellular phone via a wireless connection. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, an example being the heartbeat and its waveform.

Under prescribed conditions, the remote monitoring unit contacts a central unit to communicate information on the condition of the patient. For example, if the remote monitoring unit determines that the monitored physiological data suggests that the patient may be in distress or in an emergency condition, it may immediately and automatically transfer the monitored data to the central unit over a cellular telephone or comparable communications device. The central unit automatically, or in conjunction with medical personnel who are stationed at or are in contact with the central unit, analyzes the data and coordinates the provision of assistance to the patient when necessary. Where the analysis of the transmitted data indicates that there is no patient situation requiring immediate attention, the data is stored and may also be forwarded to the patient's physician so that treatments may be altered.

While practicable, this approach may in some cases be wasteful of the battery power of the remote monitoring unit and require the expenditure of too much data transfer time over the cellular telephone system with its associated charges. The time of the medical personnel may also be used inefficiently. Especially, today's personal health systems may cause unnecessary panic to a patient due to warning messages or warnings that the connection between two devices is not available or not properly available, while the patient's medical status may still be normal.

There is a need for an improved approach to the control of the behaviour of personal health care devices and systems, especially by reducing the number of warnings or warning messages sent to the patient or to a care giving person, while maintaining or even improving the monitoring of the patient's medical status. This increases the patient's comfort and security and thereby contributes to an even improved health status.

The above objective is accomplished by a communication system and a communication device for monitoring the health status of a patient, the communication system comprising a communication device and a sensor device, and the communication device comprising a first communication interface for communication with the sensor device and a second communication interface for communication with a health care center, the communication device being able to generate a warning message upon failure of either the first communication interface or the second communication interface, wherein the generation of a warning message is prevented if the failure of the first communication interface begins and ends during a first time interval and/or the generation of a warning message is prevented if the failure of the second communication interface begins and ends during a third time interval and/or the communication device comprises a detection device for detecting a critical or non-critical health status, and the generation of a warning message is prevented if both the duration of failure of the second communication interface is shorter than a second time interval and a non-critical health status is detected. The generation of the warning message upon failure of the first communication interface can also be done inside the sensor device. In this case, the generation of the warning message by the communication device can be regarded as the transmittal (modified or not modified) of the warning message generated by the sensor device. If the condition for suppressing the warning message or for preventing the presentation of the warning message to the patient and/or a care giving person is met, the warning message will not be transmitted to the patient and/or the care giving person.

In the context of the present invention, the terms "user" and "patient" are used almost synonymously. Furthermore, in the context of the present invention, the terms "status" and "health status" are used almost synonymously. The main application of the inventive communication device and communication system is directed to a health care application (the monitoring of the health status), but the main application may also be the monitoring of the well-being status of a user (or a patient).

An advantage of the communication system and the communication device according to the present invention is that it is possible to reduce the number of warnings or warning messages emitted towards the patient. A warning or a warning message may disturb the patient especially in the case where the patient is an elderly person who might get into a situation of panic upon receiving the warning message. Especially in the case where the emission of a warning towards the patient does not contribute to a better monitoring of the patient's health or where the emission of a warning towards the patient only slightly reduces the monitoring coverage (e.g. in terms of time intervals without monitoring available), it is advantageous according to the present invention to prevent the notification of the patient. The warning message can also be sent to a care giving person or a supervising professional. A scenario can be envisioned according to the present invention, where the communication device not only presents its warning to the patient but also sends the warning via the second communication interface to the health centre. These warnings can be used to monitor the use of the system and see if patients need help with their system. These warnings can also be (optionally) suppressed if the failure of the first communication interface does not hamper the actual transmission of data. It is also possible that a status overview (e.g. once per day or per week) of all communication issues in the communication system is sent to the health centre or the care giving person. The health centre can then contact patients with a comparably high number of communication issues or problems.

For example, a heart rate sensor used as the sensor device according to the present invention produces a heart rate value every 10 seconds and sends these values towards the communication device, e.g. a mobile telephone, a pager, a cell phone or the like. In this example, an application inside the communication device processes the received heart rate values and informs a health care center about this, especially via a GPRS connection (General packet radio system) and/or via a UMTS connection (universal mobile telephone system) and/or via a WCDMA connection and/or via a CDMA connection (code division multiple access) and/or via a 4G connection (fourth generation mobile network) and/or via a WAN connection (wide area network). In case the wireless connections between the devices of the personal health care system become unavailable (i.e. break), this can easily be detected by the communication device and/or by the sensor device. In turn, it is also comparably easy to inform a user of these devices, e.g. by means of a beep or by the blinking of an LED or by another message channel.

According to the invention, a notification of the patient or the user of the communication device and/or the sensor device is not given in all cases of such a breakdown of a communication link.

One example of such a situation concerns the communication between the sensor device and the communication device via the first communication interface. Only if the communication device does not receive data on the patient's health status with the desired frequency (i.e. defining a first time interval), an alarm or a warning message is emitted towards the user. In other cases, i.e. when the communication device receives the heart rate values, such an alarm message or warning message is suppressed or at least the transmission of such a warning message towards the user or notification of the user is prevented. In the example given, where the sensor device produces a heart rate value every 10 seconds (i.e. the first time interval) and sends these values towards the communication device, an alarm (warning message related to connectivity) will only be emitted towards the user or the patient if the communication between the sensor device and the communication device is interrupted such that at least one transmission of a heart rate value (within the exemplary frequency or transmission pattern of every 10 seconds) is omitted. Of course, in another situation, e.g. when the health status detected is dangerous or is likely to be or become dangerous, a warning message will be sent, i.e. the warning message is not suppressed.

The desired frequency (i.e. the first time interval) with which the communication device needs to receive data on the patient's health status or other information (e.g. the user's environment, the ambient temperature, the ambient air pressure, the current activity and/or posture of the patient and/or the application that is used, like fitness application, intensive care application) detected by the sensor, can be a threshold value which can be (?) adjusted by the patient and/or by the environment and/or by the health care centre. The threshold value will probably include a jitter component. This means that the measurements and/or the data that should be sent/received at a certain interval by different devices will have time differences due to unwanted variation in the internal clocks of the devices. Therefore, the threshold value preferably takes into account a certain tolerance time span (called jitter time), i.e. a deviation of the first time interval. The threshold value (determining the first time interval) preferably also comprises other components, based e.g. on the situation of the user/the patient; e.g. for a fitness application, the threshold value (i.e. the first time interval) might be larger than for an intensive care patient application. Furthermore, the threshold can be adjusted dynamically, e.g. when the situation is more dangerous or the health status of the patient becomes worse.

The same approach can apply (as one alternative of the present invention) to the communication between the communication device and the health center over the second communication interface. The third time interval also depends on the parameters determining the first time interval, but the third time interval can be different from the first time interval, i.e. the threshold value can be different.

Another example of such a situation concerns the communication between the communication device and the health care center over the second communication interface. Only in the situation where the communication device recognises that the patient's health is not normal (or that there is a certain probability that the patient's health is in a given risk range) and the communication link over the second communication interface is disturbed, a warning message is emitted towards the patient. A further warning message can be emitted according to the present invention if the duration of failure of the second communication interface is longer than a second time interval or if the failure of the second communication interface begins and ends during a third time interval.

According to the present invention, it is preferable that the communication device comprises a positioning device for determining the position of the communication device. For the purposes of the present invention, all conventionally known positioning devices can be used, either alone or in combination with one another. For example, it is possible to equip the communication device with a GPS positioning device (Global positioning system), or with a GALILEO positioning device, or with a positioning device detecting the position of the communication device by gauging the signal strength of different base stations of a cellular mobile telephone network.

The present invention also includes a sensor device for monitoring the health status of a patient and for use with a communication device and/or a communication system according to the present invention, the sensor device being provided for generating a sensor signal that is transmitted via the first communication interface to the communication device, the sensor signal comprising implicit health information as to whether the health status is critical or not. Implicit health information according to the present invention is an indication contained (implicitly) in the sensor signals transmitted towards the communication device whether the health status or medical status is normal (relative to the patient's condition, e.g. after a heart attack or the like), i.e. non-critical, or whether the medical or health status is not normal in the sense that either immediate action should be taken or in the sense that at least a state of increased alertness or vigilance (without immediate action having to be taken) is suggested by the information contained in the sensor signal. Therefore, an analysis of the sensor signals has to be done in order to extract the implicit information regarding the medical status out of the sensor signals. This can, for example, be done by simply comparing the values received in the communication device, e.g. the values representing the heart rate of the patient, with threshold values. This can also be done by complex mathematical analysis taking into account previous (stored) transmitted values, where the mathematical analysis represents a model of the normal or abnormal behaviour of the patient. Of course, further aspects can be taken into account, e.g. the patient's medical history, information from other sensors and/or sensor devices, e.g. about the user or his environment. The analysis of the sensor signals can be done inside a detection device located in the communication device. The detection device can especially be provided in the form of a software module inside the communication device.

According to the present invention, it is possible that the communication system comprises a plurality of sensor devices connected to the communication device. Nevertheless, as an exemplary embodiment of the invention, the communication system described in the following has only one sensor device.

One advantage of performing the analysis of the sensor signals in order to extract health information is that the health information does not have to be transmitted in addition to the sensor signals. This limits the need for bandwidth over the first communication interface. Furthermore, this embodiment allows for a higher degree of flexibility in analysing the sensor signals, e.g. the thresholds can be more easily adjusted, especially on demand of the health care center.

According to another embodiment of the sensor device for monitoring the health status of a patient and for use with a communication device and/or a communication system according to the present invention, the sensor device comprises the ability to perform the analysis of the sensor signals. For this purpose, the sensor device according to the other embodiment generates a sensor signal that is transmitted via the first communication interface to the communication device, the sensor signal comprising explicit health information as to whether the health status is critical or not. Therefore, the detection device inside the communication device only has to keep track of the explicit health information transmitted. This reduces the complexity of the communication device, especially if a complicated analysis of the sensor signals has to be performed requiring calculating and/or processor power that cannot be assumed to be present in a standard communication device, e.g. a mobile phone.

The present invention also includes a method of monitoring the health status of a patient, in which method a communication device and a sensor device are linked via a first communication interface, which communication device comprises a second communication interface for communication with a health care center, wherein, in a first step, a sensor signal is transferred to the communication device via the first communication interface, the sensor signal comprising health information as to whether the health status is critical or not, and the communication device is able to generate a warning message upon failure of either the first communication interface or the second communication interface, and wherein in a second step the generation of a warning message is prevented if the failure of the first communication interface begins and ends during a first time interval and/or in a second step the generation of a warning message is prevented if the failure of the second communication interface begins and ends during a third time interval and/or in a second step the health status is detected via the sensor devices and the generation of a warning message is prevented if both the duration of failure of the second communication interface is shorter than a second time interval and a non-critical health status is detected. Thereby, the interactions of the communication system with the user or the patient in case of failure or disturbances of the first and/or second communication interface can be reduced as far as possible in situations where the patient is not exposed to serious health risks. This also improves the overall behavior of the communication device and/or communication system, e.g. in terms of a longer battery life and less radiation emitted by the communication device.

Further, according to the present invention, it is preferred that the warning message is a message that is recognizable by the patient. E.g., the warning message can consist of a beep, LED-blinking, a vibration message or another optical and/or acoustical and/or haptic message.

In a preferred embodiment of the method according to the present invention, the first time interval and/or the second time interval and/or the third time interval is/are dynamically adjustable. This enables a very flexible reaction on a multitude of different situations, e.g. health degradation, whether changes and the like.

According to a preferred embodiment of the present invention, the sensor device senses the heart rate of the patient and/or the blood pressure of the patient and/or the temperature of the patient and/or the breathing rate of the patient and/or the ECG (electrocardiogram) of the patient and/or the motion of the patient and/or the galvanic skin response of the patient and/or the oxygen level of the patient and/or the blood flow of the patient and/or the acidity of the patient and/or the glucose level of the patient as an indication of the health status of the patient. Furthermore, it is possible according to the present invention that other medical or physiological parameters are sensed, e.g. the blood pressure, the temperature of the patient, physiological, psychological parameters (?) or parameters of a user's environment, e.g.: current activity, posture, stress level, ambient temperature, weather conditions, emotional state, etc. This has the advantage that the communication system can be used very flexibly and universally.

In a preferred embodiment of the method according to the present invention, the communication device monitors the signal strength of the second communication interface, and in case of the detection of a comparatively low signal strength, the patient is guided towards a first area with a sufficient signal strength. Advantageously, this enables a patient equipped with the inventive communication system and with the inventive communication device to be more effectively monitored and therefore better protected against health degradations.

In a further preferred embodiment of the method according to the present invention, the communication device stores at least one second area with a comparatively low signal strength, and the communication device detects whether the communication device is positioned inside the second area, and, if so, the patient is guided towards a first area with a sufficient signal strength. Very advantageously, this leads to a still better and more secure behavior of the inventive communication system and an inventive communication device. According to the present invention, it is also possible that the communication device periodically validates or updates the second areas (black zones) and uploads the detected updates or further second areas to a server (or a communication center).

These and other characteristics, features and advantages of the present invention will become apparent from the following detailed description, taken in conjunction with the accompanying drawings, which illustrate, by way of example, the principles of the invention. The description is given by way of example only, and should not be construed as limiting the scope of the invention. The reference figures quoted below refer to the attached drawings.

Figure 1:
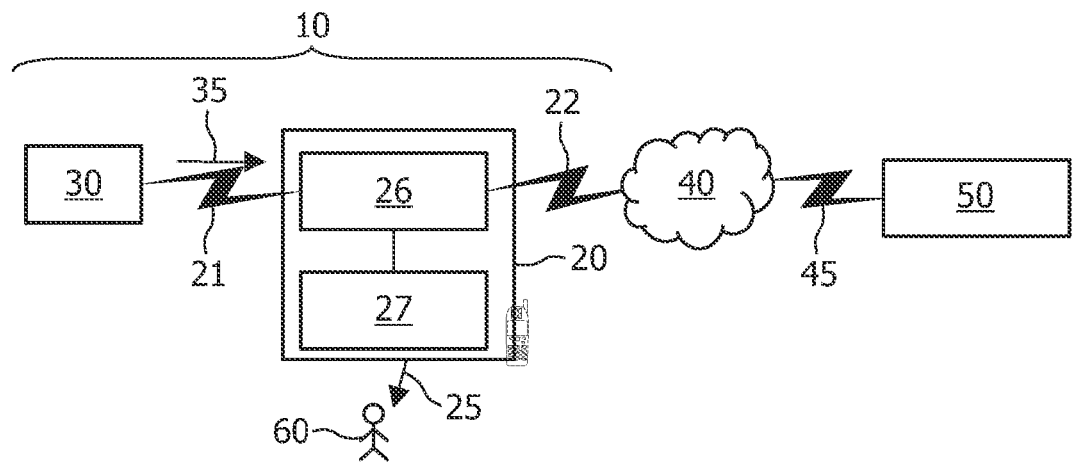
FIG. 1 illustrates schematically an inventive communication system, i.e. an inventive communication device and an inventive sensor device connected to a health care center.

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, an inventive communication system 10, i.e. an inventive communication device 20 and an inventive sensor device 30, is connected to a health care center 50. The connection between the communication device 20 and the sensor device 30 is established via a first communication interface 21 of the communication device 20 (and a corresponding communication interface on the side of the sensor device 30).

In FIG. 1, the communication link over the first communication interface 21 (i.e. between the communication device 20 and the sensor device 30) is also referred to by means of reference numeral 21. The connection between the communication device 20 and the health care center 50 is established via a second communication interface 22 of the communication device 20 (and a corresponding communication interface on the side of the health care center 50). In FIG. 1, the communication link over the second communication interface 22 (i.e. between the communication device 20 and the health care center 50) is also referred to by means of reference numeral 22. The first communication link 21 is very preferably a wireless communication link, e.g. a BLUETOOTH communication link, or a RFID (radio frequency identification) communication link, or a DECT (digital enhanced cordless telephony) communication link or a ZigBee communication link or a WiFi communication link or a Wmax communication link. The second communication link 22 is almost imperatively a wireless communication link, and very preferably a communication link using a wireless communication infrastructure 40, e.g. a mobile telephone network. In this case, where a wireless communication infrastructure 40 is used, the health care center 50 is usually connected to this communication infrastructure 40 by means of a third communication link 45. This third communication link 45 can also be a wireless communication link but usually will be a wired communication link between the communication infrastructure 40 and the health care center 50. Preferably, the second communication link 22 is a GPRS (general packet radio system) communication link or a GSM (global system for mobile telecommunication) communication link or a UMTS (universal mobile telephone system) communication link. It is also possible that the second communication link 22 is a wired communication link, e.g. between the communication device 20 as a stationary device and the health care center 50. This configuration can be used e.g. for monitoring "mobile" patients in their home environment, the patients carrying the sensor device 30 on the body and there is a wireless connection between the sensor device and the (stationary) communication device 20, e.g. a dedicated personal computer in the home. A warning message could be given if the patient goes out of the range of the wireless communication link with the stationary communication device 20. This warning should also be given on the sensor device 30 or sensor devices 30. Of course, this warning can be suppressed if the failure begins and ends during the first time interval.

The sensor device 30 is usually worn by or attached to a patient (not depicted). The sensor device 30 comprises at least a sensor means (not depicted) for determining a physiological parameter of the patient, e.g. the heart rate, the blood pressure or another physiological parameter. Therefore, the sensor means comprises for example one or a plurality of electrodes and/or one or a plurality of pressure sensors and/or one or a plurality of temperature sensors. The sensor device 30 also comprises a communication interface corresponding to the first communication interface 21 of the communication device 20 for providing the first communication link 21. Furthermore, the sensor device 30 comprises connection means (not depicted) for connecting the sensor means with the communication interface, as well as control means (not depicted) and a power supply (not depicted).

The communication device 20 is usually carried by the patient, e.g. in a trouser pocket, in a handbag, in a rucksack, in a bag, case or suitcase or in another carrying means, or it can be part of objects worn or carried by the patient, e.g. a watch, a necklace or the like. This means that the communication device 20 is usually spatially separated from the sensor device 30, but usually within a certain perimeter of the sensor device 30 of less than a few meters or less than a few tens of meters or less than a few hundreds of meters. Very preferably, the communication device 20 is provided as a mobile telephone or as a PDA (personal digital assistant) or as a laptop computer or as another portable communication device 20, but it can also be a stationary device.

The inventive communication system 10, the inventive communication device 20 and the inventive sensor device 30 aim at providing the possibility to monitor the health status of the patient in a very cost-efficient, energy-efficient, inexpensive and comfortable manner. To this end, at least one physiological parameter of the patient is monitored by means of the inventive health care communication system 10. In the following, the description of the health care communication system 10 is based primarily on the monitoring of the heart rate, but it is to be understood that other physiological parameters can also be monitored alternatively or cumulatively to the heart rate or another physiological parameter.

The heart rate, as an example of a physiological parameter to be monitored by the inventive system, is measured, or detected, by the sensor device 10 continuously or discontinuously. The values or data containing the heart rate information are transmitted via the first communication link 21 to the communication device 20 as a sensor signal 35. The sensor signal 35 is received and processed in the communication device 20 by suitable control means (not depicted). From the sensor signal 35 or from the raw data of the heart rate measurements, information evaluating or judging the health status of the patient can be derived. The result of this evaluation is hereinafter called health information. The determination of the health information implies e.g. the comparison of the currently measured or previously measured heart rate with certain threshold values, the tracking of the rate of change of the heart rate or the application of a mathematical model of a normal or abnormal development of the heart rate.

The determination of the health information can either be effected inside the sensor device 30 and/or inside the communication device 20. If the health information is determined inside the sensor device 30 (second variant), it is possible to transmit the health information as explicit health information (as the sensor signal 35 or at least as part of the sensor signal 35) towards the communication device 20. If the health information cannot be determined inside the sensor device 30 (first variant), it is only possible to transmit (as the sensor signal 35 or at least as part of the sensor signal 35) the current heart rate towards the communication device 20, where the information content of the heart rate signal (i.e. the information content of the sensor signal 35)—possibly together with knowledge of the previously measured heart rate—gives access to the health information, which means that in this case the health information is contained in an implicit form in the sensor signal 35.

In both variants of the inventive communication system 10, the communication device 20 further comprises a detection device 26 which can for example take the form of a physical circuit or part of a circuit, or a software module or a combination of software and hardware. In the first variant of the inventive communication device 20 or communication system 10 (where the health information is provided in the sensor signal 35 in its implicit form), the detection device 26 extracts from the sensor signal 35 (as raw data) the health information by effecting the above mentioned evaluation. In the second variant of the inventive communication device 20 or communication system 10 (where the health information in its explicit form is part of the sensor signal 35 transmitted to the communication device 20), the detection device 26 has access to the health information by using the transmitted explicit health information.

If a failure of the first communication link 21 or the second communication link 22 occurs, it is possible for the inventive communication system 10 to emit a warning message 25 towards the patient or the user of the communication device 20. The warning message can be an acoustic message (e.g. a beep) and/or an optic message (e.g. LED blinking) and/or a haptic message (e.g. a vibration message). The emission of a warning message 25 is very useful in the case where monitoring the health of the patient is seriously affected by a malfunction, leading to the loss of information regarding the health status of the patient. On the other hand, in situations where the monitoring of the health status of the patient is not or only unsubstantially reduced, the emission of a warning message 25 may cause unnecessary panic, disconcertment and discomfort to the patient. Furthermore, the emission of a warning message 25 leads to a higher energy consumption at least of the communication device 20, which in turn means a shorter battery life time and hence a reduction in comfort of the user.

Therefore, according to the present invention, the generation of a warning message 25 is prevented at least if the duration of failure of the first communication interface 21 begins and ends during a first time interval or if both the duration of failure of the second communication interface is shorter than a second time interval and a non-critical health status is detected.

Figure 2:
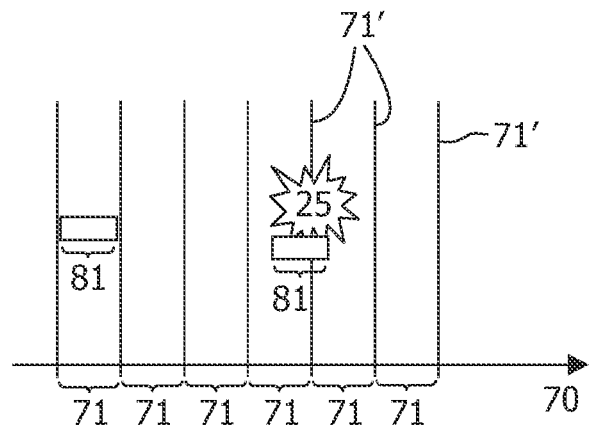
FIGS. 2 and 3 illustrate schematically the behaviour of the inventive communication system and the inventive communication device in the situation where a communication link failure occurs.
Figure 3:
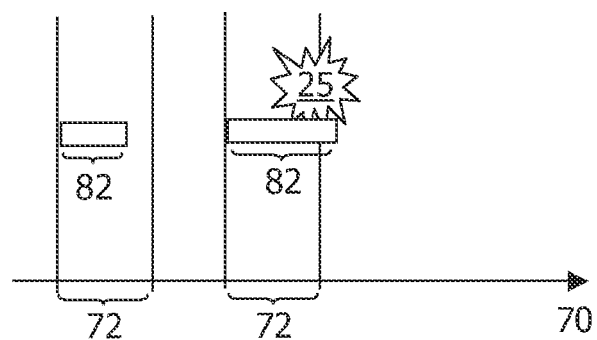

In FIGS. 2 and 3, this behavior of the inventive communication system 10 and the inventive communication device 20 is schematically depicted. FIG. 2 concerns the failure of the first communication link 21 and FIG. 3 concerns the second communication link 22. A failure of the second communication link 22 can alternatively be processed according to FIG. 1 by applying a third time interval instead of the first time interval.

In FIG. 2, on a time axis 70, a succession of a multitude of first time intervals 71 are schematically represented. This succession of first time intervals 71 correspond to a plurality of points in time 71'. According to the present invention, the first communication link 21 or the transmission of the sensor signal 35 is provided such that at all these points in time 71' the reception of the (current) sensor signal 35 is expected by the communication device 20. The emission of a warning message 25 to the patient is suppressed if there is a failure 81 of the first communication link 21 or of the first communication interface 21 which falls only in between the points in time 71' but does not disturb the transmission of the sensor signal 35 at the specified points in time 71'. This is schematically represented on the left hand side of FIG. 2, where a failure 81 of the first communication link 21 occurs but the transmission of the sensor signal 35 at the points in time 71 is not disturbed. On the right hand side of FIG. 2, an example of a failure 81 of the first communication link 21 is shown where the transmission of the sensor signal 35 at the specified points in time 71' is disturbed. In this situation, the communication system 10 detects a loss in monitoring coverage of the patient, resulting in the emission of a warning message 25 (right hand side of FIG. 2). For example, the first time interval 71 corresponds to 10 seconds, i.e. every 10 seconds a value of the heart rate is expected by the communication device 20. This means that a failure 81 of the first communication link 21 can last for a period of e.g. about 6 or about 8 or about 9 seconds, provided that no transmission of the sensor signal 35 at the specified points in time 71' is disturbed. This also means that e.g. a failure 81 of the first communication link 21 of about 1 second or about 2 seconds at one of the specified points in time 71' will result in the emission of a warning message. Of course, the first time interval 71 can be set to a different time span than about 10 seconds, e.g. about 20 second or about 30 seconds. Furthermore, the first time interval 71 can be set dynamically, e.g. depending on the detected health status of the patient.

In FIG. 3, on a time axis 70, two examples of a second time interval 72 are schematically represented. The emission of a warning message 25 to the patient is suppressed if there is a failure 82 of the second communication link 22 or of the second communication interface 22 which does not last sufficiently long. This is schematically represented on the left hand side of FIG. 3, where a failure 82 of the second communication link 22 occurs, but it does not last long enough to emit a warning message 25 to the patient. It is to be understood that this behavior (represented on the left hand side of FIG. 3) presupposes that the health information does not indicate an abnormal health status of the patient. If such an abnormal health status is indicated by the health information, a warning message 25 is emitted by the communication device 20. On the right hand side of FIG. 3, an example of a failure 82 of the second communication link 22 is shown, where the duration of that failure exceeds the second time interval 72, thus leading to the emission of a warning message 25. In this situation, the communication system 10 or the health care center 50 detects a loss in monitoring coverage of the patient, resulting in the necessity of the emission of a warning message 25 (right hand side of FIG. 3). The second time interval 72 can either be set statically (e.g. to about 30 minutes or about 5 hours) or can be set so as to be dynamically adjustable, especially dependent on the health status of the patient. It is also possible that the health care center sets the second time interval 72. Furthermore, it is also possible according to the present invention that the second time interval 72 is set to a very large value such that the warning message 25 is only emitted in cases where the health status is abnormal or critical.

In a preferred variant or embodiment of the present invention, the communication device 20 continuously monitors the signal strength of the second communication link 22 (e.g. of the GPRS-Network as an example of the network infrastructure 40 in FIG. 2). It is possible then that it is concluded that the reason for a failure 82 of the second communication interface 22 is not a breakdown of the GPRS-System, but rather the communication device 20 entering a zone of no (or weak) coverage (so-called black zone). In that case, the signal strength-monitoring device (not depicted) inside communication device 20 may advise the patient or the user of the communication system 10 to go back to an area of better signal strength. It is also possible, in a further embodiment of the present invention, that the communication device 20 is equipped with a position device 27 for determining the position of the communication device 20. Thereby, it is possible to build and store a map of the black zones such that the patient can be guided to the closest area with a higher signal strength, especially in cases where the health information indicates that the health status of the patient is no longer normal or that it is likely to degrade. In a still further embodiment of the present invention, it is also possible that zones of no or weak signal strength of the second communication link 22 are initially stored inside a memory (not depicted) of the communication device 20 or that such information is downloaded from a service provider. The information on the black zones can be gathered by means of feedback information of a multitude of users of the second communication link 22. It is also possible that the black zones are different for different models of the communication device 20.

The invention claimed is:

1. A communication device for monitoring the status of a user, comprising a first communication interface for communication with a sensor device and a second communication interface for communication with a health care center, the communication device generating a warning message upon failure of either the first communication interface or the second communication interface, wherein the communication device comprises a detection device for detecting a critical or a non-critical status, and generating the warning message is prevented if both the duration of failure of the second communication interface is shorter than a second time interval and a non-critical status is detected.

2. Communication device according to claim 1, further comprising a positioning device for determining the position of the communication device.

3. The communication device according to claim 1, wherein the generation of a warning message is prevented if the failure of the first communication interface begins and ends during a first time interval or if the failure of the second communication interface begins and ends during a third time interval.

4. The communication device according to claim 1, wherein the second time interval is dynamically adjustable.

5. The communication device according to claim 3, wherein the first time interval or the third time interval is dynamically adjustable.

6. Method of monitoring the status of a user (60), comprising:

linking a communication device and a sensor device via a first communication interface, the communication device having a second communication interface for communication with a health care center, transferring a sensor signal to the communication device via the first communication interface, the sensor signal comprising health information as to whether the status is critical or not, and generating a warning message upon failure of either the first communication interface or the second communication interface, wherein the status is detected via the sensor device and the generation of the warning message is prevented if both the duration of the failure of the second communication interface is shorter than a second time interval and non-critical status is detected.

7. Method according to claim 6, wherein the sensor device senses at least one of: a heart rate of the user, a blood pressure of the user, a temperature of the user, a breathing rate of the user, a ECG (electrocardiogram) of the user, a motion of the user, a galvanic skin response of the user, an oxygen level of the user, a blood flow of the user, an acidity of the user, a glucose level of the user as an indication of the status of the user.

8. Method according to claim 6, wherein the health information is implicit and the detection device detects the status of the user from the implicit health information by applying a detection algorithm.

9. Method according to claim 6, wherein the health information is explicit and the explicit health information is generated inside the sensor device, the sensor device detecting the status of the user by applying a detection algorithm.

10. Method according to claim 6, wherein the communication device monitors the signal strength of the second communication interface, and in case of the detection of a comparatively low signal strength, the user is guided towards a first area with a sufficient signal strength.

11. Method according to claim 6, wherein the communication device stores at least one-second area with a comparatively low signal strength, and the communication device detects whether the communication device is positioned inside the second area and, if so, the user is guided towards a first area with a sufficient signal strength.

12. A communication system for monitoring a status of a user, comprising a communication device coupled to a sensor device via a first communication interface, the communication device further comprising a second communication interface for communicating with a health care center, the communication device generating a warning message upon failure of either the first communication interface or the second communication interface, wherein the communication device includes a detection device for detecting a critical or a non-critical status, and wherein generating the warning message is prevented if 1) the duration of failure of the second communication interface is shorter than a second time interval, and 2) a non-critical status is detected.

13. The communication system according to claim 12, wherein the sensor device generates a sensor signal transmitted via the first communication interface to the communication device, the sensor signal comprising implicit health information as to whether the status is critical or not, and wherein the implicit health information is information regarding the status, which is extracted out of the sensor signal.

14. The communication system according to claim 12, wherein the sensor device generates a sensor signal transmitted via the first communication interface to the communication device, the sensor signal comprising explicit health information as to whether the status is critical or not.

* * * * *